US009822417B2

(12) United States Patent
Lothe et al.

(10) Patent No.: US 9,822,417 B2
(45) Date of Patent: Nov. 21, 2017

(54) METHODS AND BIOMARKERS FOR ANALYSIS OF COLORECTAL CANCER

(71) Applicant: OSLO UNIVERSITETSSYKEHUS HF, Oslo (NO)

(72) Inventors: Ragnhild A. Lothe, Oslo (NO); Anita Sveen, Oslo (NO); Trude Holmeide Agesen, Oslo (NO); Guro Elisabeth Lind, Oslo (NO); Arild Nesbakken, Royken (NO); Rolf Inge Skotheim, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 0 days.

(21) Appl. No.: 14/369,872

(22) PCT Filed: Jan. 9, 2013

(86) PCT No.: PCT/IB2013/000391
§ 371 (c)(1),
(2) Date: Jun. 30, 2014

(87) PCT Pub. No.: WO2013/104990
PCT Pub. Date: Jul. 18, 2013

(65) Prior Publication Data
US 2014/0342361 A1 Nov. 20, 2014

Related U.S. Application Data

(60) Provisional application No. 61/584,540, filed on Jan. 9, 2012.

(51) Int. Cl.
*C12Q 1/68* (2006.01)
*C07H 21/04* (2006.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2010/0048415 A1* | 2/2010 | Croner | C12Q 1/6886 506/9 |
| 2010/0190173 A1* | 7/2010 | Cowens | C12Q 1/6886 435/6.14 |
| 2011/0097423 A1 | 4/2011 | Beauchamp | |

FOREIGN PATENT DOCUMENTS

| | | |
|---|---|---|
| WO | 2007/082099 | 7/2007 |
| WO | 2009/052567 | 4/2009 |
| WO | 2009/140409 | 11/2009 |

OTHER PUBLICATIONS

Lin (Clin Cancer Res 2007;13(2) pp. 498-507).*
McShane (British Journal of Cancer, vol. 93, pp. 387-391, 2005).*
Coleman (Drug Discovery Today. 2003. 8: 233-235).*
Whitehead (Genome Biology 2005 vol. 6 Issue 2 Article R13).*
Chan (G&P magazine 2006 vol. 6 No. 3 pp. 20-26).*
Koshida (Cancer Sci Mar. 2007 vol. 98 No. 3 pp. 315-320).*
Mori (British Journal of Cancer 1999 vol. 79 No. 2 pp. 211-213).*
Alves (Cancer Immunity Jun. 27, 2998 vol. 8 p. 11).*
Nguyen (Mol Cancer Ther 2006 5(8) pp. 2070-2077).*
Khambata-Ford (Journal of Clinical Oncology vol. 25 No. 22 Aug. 1, 2007 pp. 3230-3237).*
Kirikoshi (International Journal of Molecular Medicine Dec. 2001 vol. 8 No. 6).*
Kasamatsu, A., et al., "Identification of candidate genes associated with salivary adenoid cystic carcinomas using combined comparative genomic hybridization and oligonucleotide microarray analyses," International Journal of Biochemistry and Cell Biology, Pergamon, GB, vol. 37, No. 9, Sep. 1, 2005, pp. 1869-1880.
Kurokawa, K., et al., "Brief naturalistic stress induces an alternative splice variant of SMG-1 lacking exon 63 in peripheral leukocytes," Oct. 29, 2010, Neuroscience Letters, Limerick, IE, pp. 128-132.
Greenbaum, D., et al., "Comparing Protein Abundance and Mrna Expressoin Levels on a Genomic Scale," Genome Biology (online), Biomed Central Ltd, GB, vol. 40, No. 9, Jan. 1, 2003, p. 117.
Greenbaum, Dov, et al., "Interrelating different types of genomic data, from proteome to secretome: Oming in on function", Genome Research, Cold Spring Harbor Laboratory Press, Woodbury, NY, US, vol. 11, No. 9, Sep. 1, 2001, pp. 1463-1468.
Oerntoft, T.F., et al., "Genome-Wide Study of Gene Copy Numbers, Transcripts, and Protein Levels in Pairs of Non-Invasive and Invasive Human Transitional Cell Carcinomas," Molecular & Cellular Proteomics, American Society for Biochemistry and Molecular Biology, Inc., US, vol. 1, No. 1, Jan. 1, 2002, pp. 37-45.
Agesen, Trude H., et al., "ColoGuideEx: a robust gene classifier specific for stage 11 colorectal cancer prognosis," Gut, British Medical Association, London, UK, vol. 61, No. 11, Jan. 2, 2012, pp. 1560-1567.
D. Besson, et al., "A Quantitative Proteomic Approach of th eDifferent Stages of Colrectal Cancer Establishes OLFM4 as a New Nonmetastatic Tumor Marker," Molecular & Cellular Proteomics, vol. 10, No. 12, Dec. 1, 2011, p. 1429.
Tatoh et al. "Integrative genomic analyses of WNT11: Transcriptional mechanisms based on canonical WNT signals and GATA transcription factors" International Journal of Molecular Medicine, 2009, vol. 24, pp. 247-251.
Kirikoshi et al. "Molecular cloning and characterization of human WNT11" International Journal of Molecular Medicine, 2001, vol. 8, pp. 651-656.
Watanabe et al. "Predicting Ulcerative Colitis-Associated Colorectal Cancer Using Reverse-Transcription Polymerase Chain Reaction Analysis" Clinical Colorectal Cancer, 2011, vol. 10, No. 2, pp. 134-141.

(Continued)

*Primary Examiner* — Amanda Haney
(74) *Attorney, Agent, or Firm* — Casimir Jones S.C.

(57) ABSTRACT

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics.

2 Claims, 5 Drawing Sheets

(56) References Cited

OTHER PUBLICATIONS

Mlecnik et al. "Biomolecular Network Reconstruction Identifies T-Cell Homing factors Associated with Survival in Colorectal Cancer" Gastroenterology, 2011, vol. 138, pp. 1429-1440.
Robbe et al. "DMBT1 expression and glycosylation during the adenoma-carcinoma sequence in colorectal cancer" Biochemical Society Transactions, 2005, vol. 33, part 4, pp. 730-732.
Kang et al. "Induction of DMT1 expression by reduced ERK activity during a gastric mucosa differentiation-like process and its association with human gastric cancer" Carcinogenesis, 2005, vol. 296, No. 6, pp. 1129-1113.

\* cited by examiner

Figure 6
Stage II                                   Stage III
A  Relapse-free survival      B  Relapse-free survival
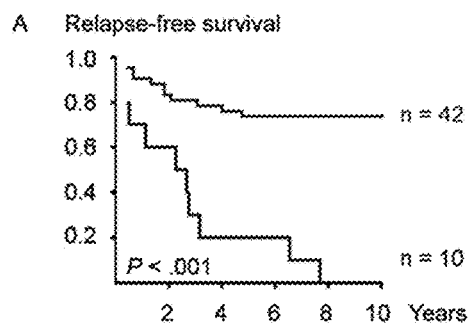
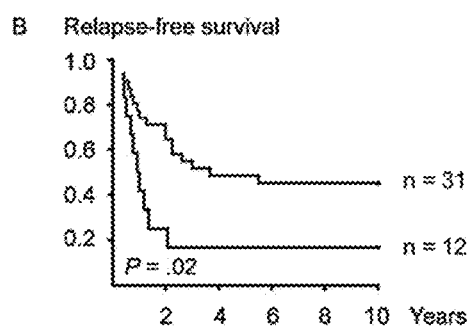
C  Relapse-free survival      D  Relapse-free survival
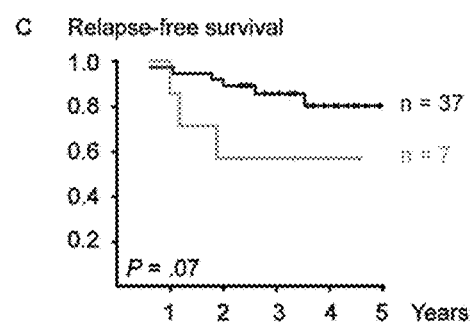
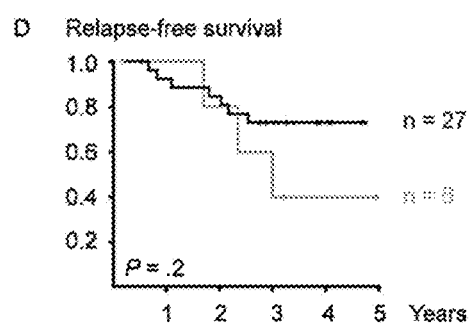
E  Relapse-free survival      F  Relapse-free survival
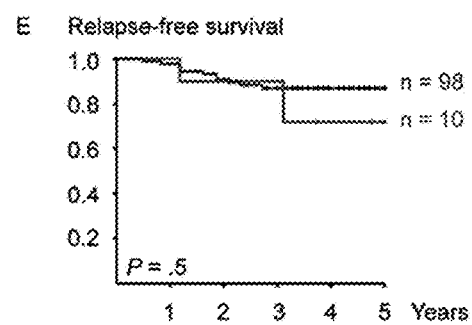
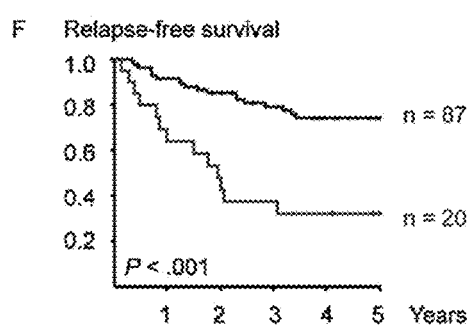
Gene expression signature:
▬ Good prognosis
▬ Poor prognosis, test series
▭ Poor prognosis, validation series I
▬ Poor prognosis, validation series II Figure 7
Stage II CRC (n = 19):
Stage III CRC (n = 20):
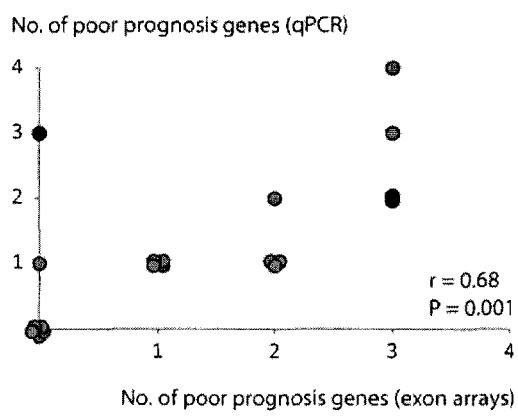
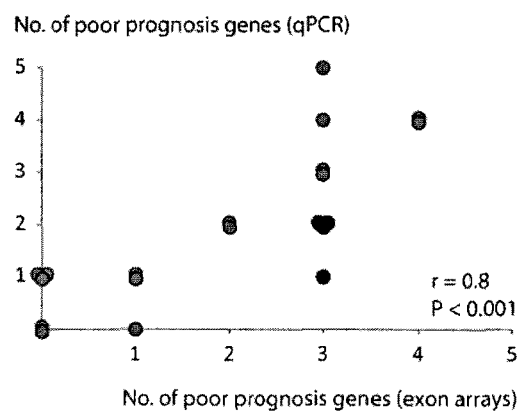
● Identically classified samples
● Differently classified samples

METHODS AND BIOMARKERS FOR ANALYSIS OF COLORECTAL CANCER

CROSS-REFERENCE TO RELATED APPLICATIONS

The present application is a Section 371 U.S. national stage entry of pending International Patent Application No. PCT/IB2013/000391, International Filing Date Jan. 9, 2013, which published on Jul. 18, 2013 as Publication No. WO 2013/104990, which claims the benefit of U.S. Provisional Patent Application No. 61/584,540, filed Jan. 9, 2012, the contents of which are incorporated by reference in its entirety.

FIELD OF THE INVENTION

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics.

BACKGROUND OF THE INVENTION

Colorectal cancer (CRC) is the third most common type of cancer with a worldwide annual incidence of 1.2 million, and mortality rate of approximately 50%. The only available curative treatment for CRC is complete surgical resection of neoplastic tissue (Van Cutsem et al., Colon cancer: Management of locoregional disease, in Kelsen D P, Daly J M, Kern S E, et al (ed): Principles and practice of gastrointestinal oncology. Philadelphia, USA, Lippincott Williams & Wilkins, 2008, pp 581). Determination of the extent of the disease by clinicopathological tumor staging is the primary prognostic factor for CRC patients (Van Cutsem et al., supra). Despite the favorable outcome for patients with localized stage II tumors compared to stage III tumors, more than 20% of stage II patients suffer from recurrence (Gray et al., Lancet 370:2020-2029, 2007). Still, investigations of benefit from adjuvant chemotherapy for stage II patients show conflicting results (Andre et al., Ann Surg Oncol 13:887-898, 2006; Sobrero A, Lancet Oncol 7:515-516, 2006; Kohne, Lancet Oncol 7:516-517, 2006), and surgery remains the only recommended treatment modality (Benson et al., J Clin Oncol 22:3408-3419, 2004). For patients with stage III disease, large clinical trials have consistently showed improved survival with administration of adjuvant chemotherapy, and this constitutes the standard of care for this group of patients (Andre et al., N Engl J Med 350:2343-2351, 2004). However, the significantly poorer survival among patients with stage IIB (T-stage 4, lymph node negative) compared to stage IIIA (T-stage 1-2, lymph node positive) disease, underlines the need for refinements to this prognostic stratification (O'Connell et al., J Natl Cancer Inst 96:1420-1425, 2004).

Accordingly, identification of individual patients in need of adjuvant treatment, primarily by predicting prognosis for stage II and III patients remains a major clinical concern. There are currently no markers in routine clinical use for this purpose (Locker et al., ASCO 2006 J Oncol Pract 24:5313-5327, 2006). Hence, identification of molecular markers for prognostic stratification represents a valuable step towards beneficial personalized management of patients with stage II and III disease.

SUMMARY OF THE INVENTION

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics.

For example, in some embodiments, the present invention provides a method for determining a prognosis of colorectal cancer in a subject, diagnosing a colorectal cancer in a subject, predicting a predisposition to colorectal cancer in a subject, predicting the likelihood of recurrence of colorectal cancer in a subject, or selecting a subject with a disease for treatment with a particular therapy, comprising: a) contacting a biological sample from a subject diagnosed with colorectal cancer with a reagent for detecting the level of expression of one or more, two or more, three or more, four or more, five or more, or all seven genes selected from, for example, OLFM4, CXCL9, DMBT1, UGT2B17, SEMA3A, NT5E, or WNT11; and b) detecting the level of expression of the genes using an in vitro assay, wherein an altered level of expression of said one or more genes provides: an indication of a poor prognosis of the subject, a diagnosis of a colorectal cancer in the subject, a prediction of a predisposition to colorectal cancer in the subject, a prediction of the likelihood of recurrence of colorectal cancer in the subject, or an indication that the subject is a candidate for treatment with a particular therapy. In some embodiments, the one or more genes comprises a set of two or more, three or more, four or more, five or more, six or more, or all seven genes selected from one of (OLFM4 or CLCA1), one of (CXCL9 or GBP5), one of (DMBT1 or REG1A), one of (UGT2B17 or ADH1C), one of (SEMA3A or HAS2), one of (NT5E or SLC35A1), or one of (WNT11 or PMEPA1). In some embodiments, the genes comprise the set of OLFM4, CXCL9, DMBT1, UGT2B17, SEMA3A, NT5E, and WNT11. In some embodiments, the biological sample is a tissue sample, a biopsy sample, a blood sample or a stool sample. In some embodiments, the subject has been previously diagnosed with colorectal cancer.

In some embodiments, a decreased level of expression of one or more genes selected from one of (OLFM4 or CLCA1), one of (CXCL9 or GBP5), or one of (UGT2B17 or ADH1C) relative to a reference level of expression of the genes is associated with a poor prognosis of the subject. And/or an increased level of expression of one or more genes selected one of (DMBT1 or REG1A), one of (SEMA3A or HAS2), one of (NT5E or SLC35A1), or one of (WNT11 or PMEPA1) relative a reference level of expression of the genes is associated with a poor prognosis of the subject. In some embodiments, the poor prognosis comprises decreased survival or recurrence or metastasis of the colorectal cancer. In some embodiments, the reference level is a level from a subject diagnosed with colorectal cancer or a subject not diagnosed with colorectal cancer. In some embodiments, the prognosis 5 year relapse free survival.

In some embodiments, the method further comprises the step of determining a treatment course of action (e.g., including but not limited to, administering chemotherapy to subjects identified as having a poor prognosis and not administering chemotherapy to subjects identified as having a good prognosis). In some embodiments, the chemotherapy is adjuvant chemotherapy.

In some embodiments, the colon cancer is stage I, II or III. In some embodiments, the colorectal cancer informative reagent is, for example, a nucleic acid probe or probes that hybridizes to a respective gene product of the one or more genes, nucleic acid primers for the amplification and detection of a respective gene product of the one or more genes, or an antigen binding protein specific for a respective gene product of the one or more genes. In some embodiments, the gene product is an RNA transcript from the gene and the colorectal informative reagent is a nucleic acid probe or probes that hybridizes to the respective gene product of the one or more genes or nucleic acid primers for the amplification and detection of the respective gene product of the one or more genes.

In some embodiments, the present invention provides a method for diagnosing colorectal cancer in a subject, comprising: a) contacting a biological sample from a subject with a colorectal cancer informative reagent for detecting the level of expression of one or more genes selected from, for example, one of (OLFM4 or CLCA1), one of (CXCL9 or GBP5), one of (DMBT1 or REG1A), one of (UGT2B17 or ADH1C), one of (SEMA3A or HAS2), one of (NT5E or SLC35A1), or one of (WNT11 or PMEPA1); and b) detecting the level of expression of the one or more genes using the colorectal cancer informative reagent in an in vitro assay, wherein an altered level of expression of the one or more genes is indicative of a poor prognosis related to colorectal cancer in the subject.

In still further embodiments, the present invention provides a kit, comprising: one or more, two or more, three or more, four or more, five or more, six or more, or seven colorectal informative reagents for detecting altered gene expression in a sample from a subject having or suspected of having colorectal cancer of one or more, two or more, three or more, four or more, five or more, six or more, or all seven genes selected from, for example, (OLFM4 or CLCA1), one of (CXCL9 or GBP5), one of (DMBT1 or REG1A), one of (UGT2B17 or ADH1C), one of (SEMA3A or HAS2), one of (NT5E or SLC35A1), or one of (WNT11 or PMEPA1). In some embodiments, the genes comprise the set of OLFM4, CXCL9, DMBT1, UGT2B17, SEMA3A, NT5E, and WNT11. In some embodiments, the one or more colorectal informative reagents are, for example, a probe(s) that specifically hybridizes to a respective gene product(s) of the one or more genes, a set(s) of primers that amplify a respective gene product(s) of the one or more genes, an antigen binding protein(s) that binds to a respective gene product(s) of the one or more genes, or a sequencing primer(s) that hybridizes to and allows sequencing of a respective gene product(s) of said one or more genes.

Further embodiments of the present invention provide the use of any of the aforementioned kits for determining a prognosis of a subject diagnosed with colorectal cancer, diagnosing colorectal cancer in a subject, or determining the likelihood of success of a specific treatment and/or selecting patient for the treatment.

Additional embodiments will be apparent to persons skilled in the relevant art based on the teachings contained herein.

DESCRIPTION OF THE DRAWINGS

FIG. 6. Survival curves in each stage for patients in the three independent series. Stage II (left) and III (right) CRC patients were individually stratified according to the 7-gene expression signature. In the test series, A) stage II patients with good and poor prognosis had significantly different 10-year relapse-free survival rates (74% and 0%, respectively; HR=6.6 [2.7, 16.1]). The corresponding survival rates for B) stage III tumors were 45% and 17%, respectively (HR=2.6 [1.2, 5.7]). In validation series I, C) good prognosis patients with stage II tumors had a 5-year relapse-free survival rate of 80%, compared to 57% for patients with poor prognosis (HR=3.3 [0.8, 13.3]). The corresponding survival rates in D) stage III patients were 73% and 40%, respectively (HR=2.3 [0.6 to 8.8]). Patients in validation series II with E) stage II tumors were divided into good and poor prognosis groups with 5-year relapse-free survival rates of 87% and 72%, respectively (HR=1.8 [0.4, 7.9]). The corresponding survival rates for patients with F) stage III tumors were 74% and 32%, respectively (HR=4.1 [2.0, 8.3]).

FIG. 7. Demonstration of correlation between qPCR and exon microarray data in the sample-wise number of genes in ColoGuidePro being expressed at levels associated with poor prognosis.

DEFINITIONS

Figure 1:
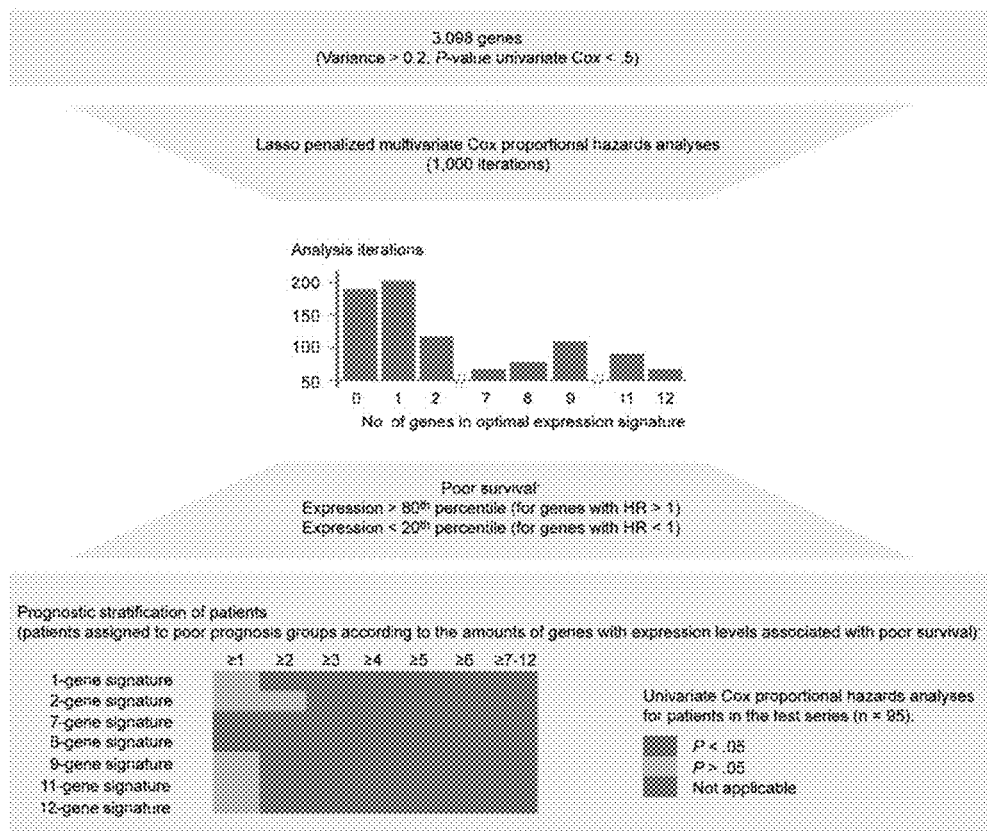
FIG. 1. Analysis workflow for development of the prognostic gene expression signature. From the test series of 95 stage II and III CRC samples, a filtered gene expression dataset was used as input for survival modeling. From 1,000 iterations of lasso penalized multivariate modeling, eight models were reported as optimal for survival prediction more than 50 times (middle bar plot). For each of the gene expression signatures, patients were dichotomized to good and poor prognosis groups according to all the possible stepwise increases in amounts of genes being expressed at levels associated with poor survival (lower panel). All 28 possible stratifications were tested for univariate associations with patient survival, yielding significant associations for 22 (79%; dark blue; hazard ratio (HR) ranging from 3.0 to 11.5).

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the terms "colorectal cancer informative reagent" refers to a reagent or reagents that are informative for identification of expression of cancer gene markers described herein. In some embodiments, reagents are primers, probes or antibodies for detection of gene expression products (e.g., RNA transcripts or proteins) of the following genes: OLFM4, CXCL9, DMBT1, UGT2B17, SEMA3A, NT5E, or WNT11.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized colorectal cancer cells" is meant to refer to colorectal cancer cells which have metastasized; colorectal cancer cells localized in a part of the body other than the colorectal.

As used herein, "an individual is suspected of being susceptible to metastasized colorectal cancer" is meant to refer to an individual who is at an above-average risk of developing metastasized colorectal cancer. Examples of individuals at a particular risk of developing colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "colorectal neoplasm-specific marker" refers to any biological material that can be used to indicate the presence of a colorectal neoplasm (e.g., a premalignant colorectal neoplasm, a malignant colorectal neoplasm, a metastatic colorectal neoplasm). Examples of colorectal neoplasm-specific markers include, but are not limited to, the 13 gene signature described herein.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "locus" as used herein refers to a nucleic acid sequence on a chromosome or on a linkage map and includes the coding sequence as well as 5' and 3' sequences involved in regulation of the gene.

DETAILED DESCRIPTION OF THE INVENTION

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics.

Adjuvant chemotherapy significantly improves survival in stage III CRC and is accepted as standard treatment of these patients. The majority of stage II CRC patients are cured by surgery alone, but there are indications that the proportion of stage II patients who still develop relapse would benefit from adjuvant chemotherapy. This highlights the need for biomarkers for more precise prediction of high risk stage II patients, and consequently also improved individualized cancer care. On the other hand, there are patients in stage III that will be cured by surgery alone and should not receive adjuvant chemotherapy. If they were pinpointed at time of diagnosis severe side effects could be avoided improving quality of life for the patient.

Prognostic gene expression signatures have shown predictive value in cancer management, primarily for patients with breast cancer (Glas et al., BMC Genomics 7:278, 2006). Also for CRC, several studies have reported prognostic gene expression signatures, focusing primarily on stage II and III tumors (Arango et al., Gastroenterology 129:874-884, 2005; Barrier et al., J Clin Oncol 24:4685-4690, 2006; Bertucci et al., Oncogene 23:1377-1391, 2004; Eschrich et al., J Clin Oncol 23:3526-3535, 2005; Wang et al., J Clin Oncol 22:1564-1571, 2004). However, these studies have generally been limited by small sample sizes and/or lack of testing in independent sample series (Lu et al., Clin Colorectal Cancer 8:207-214, 2009). More recently, larger studies have shown potential prognostic predictive value for gene expression signatures of varying sizes (Jorissen et al., Clin Cancer Res 15:7642-7651, 2009; O'Connell et al., J Clin Oncol 28:3937-3944, 2010; Salazar et al., J Clin Oncol 29:17-24, 2011; Smith et al., Gastroenterology 138: 958-968, 2010). However, no studies have considered the abundance of prognostic information contained within the proposed signatures, possibly resulting in unnecessary large signatures and reduced robustness due to increased risk of over-fitting. Furthermore, testing of independent prediction potential has generally been limited to only one patient series.

Experiments conducted during the course of developments of embodiments of the present invention developed a non-redundant prognostic gene signature for stage II and III CRC based on the expression of seven genes using variable selection by $L_1$ (lasso) penalization and cross-validation in the Cox proportional hazards model (Goeman et al., Biom J 52:70-84, 2009). The prognostic value of this signature was positively validated in two independent patient series analyzed on different microarray platforms. The expression signature was also a significant predictor of poor prognosis independent of tumor stage and various other clinicopathological parameters in both the test series and the two independent validation series.

Accordingly, in some embodiments, the present invention provides a set of one or more genes which, together, predicts the diagnosis and prognosis for patients with stage II and III colorectal cancer. This expression signature is a significant predictor of poor prognosis both in the test series and two independent validation series analyzed on different microarray platforms. Also, prognostic stratification is independent of tumor staging and other clinicopathological parameters. The genes in the set are one or more of OLFM4, CXCL9, DMBT1, UGT2B17, SEMA3A, NT5E, and WNT11.

The 7-gene expression signature reported here is among the smallest reported for prognostic stratification of stage II and III CRC patients. Previously published signatures have typically contained a rather large number of genes, ranging from 23 to several hundred, and there has been little focus on the implications of this during development of the survival models (Arango et al., supra; Barrier et al., supra; Bertucci et al., supra; Eschrich et al., supra; Wng et al., supra; Jorissen et al. supra; Smith et al. supra). A major statistical concern regarding prognostic prediction based on gene expression profiles relates to the high-dimensionality of the data. Over-fitting of large and complex gene expression models to the limited heterogeneity represented within the test set of tumors, compromises the independent predictive powers. This risk can be reduced by penalization of the gene expression data using parameters tuned during cross-validation (van Houwelingen et al., Stat Med 25:3201-3216, 2006). In this study, lasso was used for penalization and simultaneous variable selection (Goeman, Biom J 52:70-84, 2009; Tibshirani J R Statist Soc B 58:267-288, 1996; Tibshirani, Stat Med 16:385-395, 1997). Iterations of lasso modeling in the test series resulted in several models accommodating optimal penalty conditions, illustrating the difficulty in predicting prognostic value in independent samples. To ensure independent prediction value, selection of the presented 7-gene signature over the other proposed models from the test series, was aided by testing independent samples in validation series I.

Prospective testing of prediction models in large clinical trials provides a powerful means for assessment of their prognostic value. Currently, a phase III clinical trial is recruiting patients for the assessment of the ColoPrint test in stage II CRC patients (PARSC-study) (PARSC study (NCT00903565): A prospective study for the assessment of recurrence risk in stage II colon cancer patients using ColoPrint (PARSC), 2010). ColoPrint, an 18-gene expression-based prognostic predictor for stage II and III CRC, has recently been validated in an independent patient series (univariate HR=2.5; P=0.005) (Salazar et al., J Clin Oncol 29:17-24, 2011). Another test, Oncotype DX, is a 12-gene recurrence predictor for stage II CRC (Genomic Health, I: Oncotype DX colon cancer assay, 2011), developed from analyses of preselected genes in more than 1,800 patients across four studies (O'Connell et al., J Clin Oncol 28:3937-3944, 2010). Its predictive value has been tested on patients recruited from the QUASAR-study (Gray et al., supra), but despite reports of positive results in this initial validation study (Kerr et al., J Clin Oncol 27:4000, 2009), more evidence is needed for a full evaluation of its value in clinical practice (Webber et al., PLoS Curr 2:RRN1177, 2010). Although these tests are based on the expression levels of small numbers of genes, there are indications of covariation within the signatures (Pearson correlations of expression values up to 0.70 and 0.88 for gene pairs within the ColoPrint and Oncotype DX tests, respectively, as analyzed in the test series of stage II and III CRCs in the current study; $P<0.0001$). In this study, and in accordance with the lasso model, the seven proposed genes have only weak correlations to each other (strongest Pearson correlation 0.55). Hence, there is little redundancy in the signature, and reduced covariation improves the independent prediction potential of the individual genes (Nxs et al., J Chemom 15:413-426, 2001).

The strong and significant stratification of patients according to survival seen in two independent series here, in addition to the test series, is comparable to what has been reported for gene expression signatures in single validation series in previous studies (Jorissen et al., supra; O'Connell et al., supra; Salazar et al., supra; Smith et al., supra). The external validation series II is a collection of data from two of these studies (Jorissen et al., supra; Smith et al., supra), and include the two major datasets with corresponding clinical information that are available from public repositories. These samples were analyzed on gene-level microarrays (Affymetrix HG-U133 Plus2.0), whereas the two in-house datasets were analyzed by exon-level microarrays (Affymetrix GeneChip Human Exon 1.0 ST). The good performance of the 7-gene expression signature in validation series analyzed on both types of microarrays indicates robustness. More reliable expression measures in the test series, with large numbers of probes targeting each gene across the entire length of the expressed sequences, may have contributed to this.

The 7-gene expression signature was developed from a historical series of CRC patients not treated with adjuvant chemotherapy. The signature was also found to perform well also on patients treated according to the current treatment regime. In multivariate models including e.g. tumor stage, the signature was an independent predictor of prognosis in all three patient series.

Clinically useful prognostic tests should not require heavy resources in terms of expression measures and subsequent interpretation of results (Koscielny, Sci Transl Med 2:14ps2, 2010; Haibe-Kains et al., Bioinformatics 24:2200-2208, 2008). The genes selected for the 7-gene signature have high variances in expression signals, increasing the reliability of differential expression measures. Also, stratification of patients is based on the simple principle of summarizing the number of genes expressed outside a threshold value. This strategy resulted in similar prognostic stratification when comparing with computation of PI's based on multivariate regression coefficients estimated as an inherent part of the lasso survival model. This indicates that the simple stratification rule proposed here is a valid replacement for a commonly used, but more complex mathematical model.

I. Diagnostic and Screening Methods

As described above, embodiments of the present invention provide diagnostic, prognostic and screening methods that utilize the detection of altered levels of expression of cancer marker genes (e.g., OLFM4, CXCL9, DMBT1, UGT2B17, SEMA3A, NT5E, or WNT11) and combinations thereof. In some embodiments, the methods and kits utilize or enable detection of altered gene expression in a subject of one or more, two or more, three or more, four or more, five or more, six or more, or all seven cancer marker genes selected from OLFM4, CXCL9, DMBT1, UGT2B17, SEMA3A, NT5E, or WNT11. In some embodiments, the methods and kits utilize or enable detection of altered gene expression in a subject of one or more, two or more, three or more, four or more, five or more, six or more, or all seven cancer marker genes selected from OLFM4, CXCL9, DMBT1, UGT2B17, SEMA3A, NT5E, or WNT11. In some embodiments, the methods and kits utilize or enable detection of altered gene expression in a subject of two or more, three or more, four or more, five or more, six or more, or all seven cancer marker genes selected from one of (OLFM4 or CLCA1), one of (CXCL9 or GBP5), one of (DMBT1 or REG1A), one of (UGT2B17 or ADH1C), one of (SEMA3A or HAS2), one of (NT5E or SLC35A1), or one of (WNT11 or PMEPA1). In some embodiments, the methods and kits utilize colorectal cancer informative reagents for the detection of a gene product (e.g., RNA transcript or protein or one or more, two or more, three or more, four or more, five or more, 6 or more, or all seven of the marker genes listed in column A of Table 1. In some embodiments, one or more of the cancer marker genes listed in column B of table 1 may be substituted for the corresponding cancer marker gene in column A and the appropriate colorectal cancer informative reagent may be utilized in the method or kit.

Exemplary, non-limiting embodiments are described below.

TABLE 1

|  | Column A | Column B |
| --- | --- | --- |
| ColoGuidePro | OLFM4 | CLCA1 |
|  | CXCL9 | GBP5 |
|  | DMBT1 | REG1A |
|  | UGT2B17 | ADH1C |
|  | SEMA3A | HAS2 |
|  | NT5E | SLC35A1 |
|  | WNT11 | PMEPA1 |

Any patient sample suspected of containing the genes may be tested according to methods of embodiments of the present invention. By way of non-limiting examples, the sample may be tissue (e.g., a colorectal biopsy sample or other tissue sample), blood, stool or a fraction thereof (e.g., plasma, serum, etc.).

In some embodiments, the patient sample is subjected to preliminary processing designed to isolate or enrich the sample for the pseudogenes or cells that contain the pseudogenes. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

While the present invention exemplifies several markers specific for detecting and providing a prognosis for colorectal cancer, any marker that is correlated with the presence or absence of colorectal cancer may be used, alone or in combination with the markers described herein. A marker, as used herein, includes, for example, nucleic acid(s) whose production or mutation or lack of production is characteristic of a colorectal neoplasm or a prognosis thereof. Depending on the particular set of markers employed in a given analysis, the statistical analysis will vary. For example, where a particular combination of markers is highly specific for colorectal cancer, the statistical significance of a positive result will be high. It may be, however, that such specificity is achieved at the cost of sensitivity (e.g., a negative result may occur even in the presence of colorectal cancer). By the same token, a different combination may be very sensitive (e.g., few false negatives, but has a lower specificity).

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action. Markers for other cancers, diseases, infections, and metabolic conditions are also contemplated for inclusion in a multiplex or panel format.

The methods are not limited to a particular type of mammal. In some embodiments, the mammal is a human. In some embodiments, the colorectal neoplasm is premalignant. In some embodiments, the colorectal neoplasm is malignant. In some embodiments, the colorectal neoplasm is colorectal cancer without regard to stage of the cancer (e.g., stage I, II, III, or IV). In some embodiments, the colorectal cancer is stage II.

A. DNA and RNA Detection—Colorectal Cancer Informative Reagents

The cancer marker genes of the present invention are detected using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art, See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, deep sequencing is utilized to provide an analysis of the sequence and frequency of RNA molecules in the samples. Suitable deep sequencing techniques include, but are not limited to, next generation sequencing techniques such as single molecule real time sequencing (Pacific Biosciences), sequencing by synthesis (Illumina, Inc.), 454 pyrosequencing (Roche Diagnostics, Inc.), SOLiD sequencing (Life Technologies, Inc.), and ion semiconductor sequencing (Life Technologies, Inc.).

In some embodiments, second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. are utilized. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques including fluorescence-based sequencing methodologies (See, e.g., Birren et al., Genome Analysis: Analyzing DNA, 1, Cold Spring Harbor, N.Y.; herein incorporated by reference in its entirety) find use in embodiments of the present invention. In some embodiments, parallel sequencing of partitioned amplicons (PCT Publication No: WO2006084132 to Kevin McKernan et al., herein incorporated by reference in its entirety) is utilized. In some embodiments, DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties) is utilized. Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing (see, e.g., Astier et al., J. Am. Chem. Soc. 2006 Feb. 8; 128(5):1705-10, herein incorporated by reference) it utilized. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences (Voelkerding et al., Clinical Chem., 55: 641-658, 2009; MacLean et al., Nature Rev. Microbiol., 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety) is utilized. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescentlylabeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

In some embodiments, the nucleic acid sequencing approach developed by Stratos Genomics, Inc. and involves the use of Xpandomers is utilized. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., pseudogenes) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, gene expression is detected using fluorescence in situ hybridization (FISH). In some embodiments, FISH assays utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human colorectal cells, human colorectal tissue or on the fluid surrounding said human colorectal cells or tissue. Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., Am. J. Hum. Genet. 49:112-119 (1991); Klinger, et al., Am. J. Hum. Genet. 51:55-65 (1992); and Ward, et al., Am. J. Hum. Genet. 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

In some embodiments, the present invention utilizes nuclease protection assays. Nuclease protection assays are useful for identification of one or more RNA molecules of known sequence even at low total concentration. The extracted RNA is first mixed with antisense RNA or DNA probes that are complementary to the sequence or sequences of interest and the complementary strands are hybridized to form double-stranded RNA (or a DNA-RNA hybrid). The mixture is then exposed to ribonucleases that specifically cleave only single-stranded RNA but have no activity against double-stranded RNA. When the reaction runs to completion, susceptible RNA regions are degraded to very short oligomers or to individual nucleotides; the surviving RNA fragments are those that were complementary to the added antisense strand and thus contained the sequence of interest. Suitable nuclease protection assays, include, but are not limited to those described in U.S. Pat. No. 5,770,370; EP 2290101A3; US 20080076121; US 20110104693; each of which is incorporated herein by reference in its entirety. In some embodiments, the present invention utilizes the quantitative nuclease protection assay provided by HTG Molecular Diagnostics, Inc. (Tucson, Ariz.).

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., genes described herein) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jetprinting; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Nucleic acids (e.g., cancer marker genes) may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and U.S. Pat. No. 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified nucleic acids can be detected by any conventional means. For example, the cancer marker genes described herein can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

B. Protein Detection—Colorectal Cancer Informative Reagents

The cancer marker genes described herein may be detected as proteins using a variety of protein techniques known to those of ordinary skill in the art, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

II. Data Analysis

In some embodiments, a computer-based analysis program is used to translate the raw data generated by the detection assay (e.g., the expression level a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or stool sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., prognosis of disease free survival or metastasis) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

III. Compositions & Kits

Compositions for use in the diagnostic methods described herein include, but are not limited to, kits comprising one or more colorectal cancer informative reagents as described above. In some embodiments, the kits comprise one or more colorectal cancer informative reagents for detecting altered gene expression in a sample from a subject having or suspected of having colorectal cancer of one or more, two or more, three or more, four or more, five or more, six or more, or all seven cancer marker genes selected from one of (OLFM4 or CLCA1), one of (CXCL9 or GBP5), one of (DMBT1 or REG1A), one of (UGT2B17 or ADH1C), one of (SEMA3A or HAS2), one of (NT5E or SLC35A1), or one of (WNT11 or PMEPA1).

In some embodiments, the kits contain colorectal cancer informative reagents specific for a cancer gene marker, in addition to detection reagents and buffers. In preferred embodiments, the colorectal informative reagent is a probe(s) that specifically hybridizes to a respective gene product(s) of the one or more genes, a set(s) of primers that amplify a respective gene product(s) of the one or more genes, an antigen binding protein(s) that binds to a respective gene product(s) of the one or more genes, or a sequencing primer(s) that hybridizes to and allows sequencing of a respective gene product(s) of the one or more genes. The probe and antibody compositions of the present invention may also be provided in the form of an array. In preferred embodiments, the kits contain all of the components necessary to perform a detection assay, including all controls, directions for performing assays, and any necessary software for analysis and presentation of results.

In some embodiments, the kits include instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

III. Methods of Use

As disclosed herein, the present invention provides colorectal cancer informative reagents and methods for determining a prognosis of colorectal cancer in a subject, diagnosing a colorectal cancer in a subject, predicting a predisposition to colorectal cancer in a subject, predicting the likelihood of recurrence of colorectal cancer in a subject, or selecting a subject with a disease for treatment with a particular therapy. The colorectal cancer can be stage I, II, III, or IV colorectal cancer. In some preferred embodiments, embodiments of the present invention provide compositions and methods for providing a prognosis to a patient diagnosed with colorectal cancer (e.g., stage II colorectal cancer). For example, in some embodiments, altered expression relative to a control sample (e.g., non-cancerous colorectal tissue or stage I or IV colorectal cancer) of one or more of OLFM4, CXCL9, DMBT1, UGT2B17, SEMA3A, NT5E, or WNT11 is associated with a poor prognosis. In particular, in some embodiments, a decreased level of expression of one or more of one of (OLFM4 or CLCA1), one of (CXCL9 or GBP5), or one of (UGT2B17 or ADH1C), and/or an increased level of expression of one of (DMBT1 or REG1A), (SEMA3A or HAS2), one of (NT5E or SLC35A1), or one of (WNT11 or PMEPA1) relative to a reference level of expression in a control sample of the genes is associated with a poor prognosis (e.g., decreased survival or increased risk of metastasis). In some embodiments, the reference level is from a subject diagnosed with stage I or IV colorectal cancer. In some embodiments, the reference level is from a subject not diagnosed with colorectal cancer. In some embodiments, the level of expression as compared to the reference level is indicative of a poor prognosis. In some embodiments, the poor prognosis is a decreased chance of survival. In some embodiments, the poor prognosis is an increased chance of recurrence or metastasis of colorectal cancer. In some embodiments, the prognosis is the likelihood of 5 year relapse free survival.

In some embodiments, the prognostic information is used to determine a treatment course of action for the subject. For example, in some embodiments, subjects found to have a poor prognosis can be given adjuvant chemotherapy, while subjects with a good prognosis can be treated with surgery alone. In further embodiments, the assays of the present invention are utilized during clinical testing of therapeutic agents for colorectal cancer. It is contemplated that the assays for gene products as described above will define specific patient populations for which treatment with the therapeutic agent is more or less effective than the patient population as a whole. Thus, in some embodiments of the present invention, methods are provided where subjects are screened using the assays of the present invention and patients with a particular profile of gene expression as described above are selected for treatment with a particular therapeutic agent or therapeutic regime.

EXPERIMENTAL

The following examples are provided in order to demonstrate and further illustrate certain preferred embodiments and aspects of the present invention and are not to be construed as limiting the scope thereof Example 1

Materials and Methods

Altogether 172 fresh frozen stage II and III CRC tissue samples from two independent patient series were analyzed in the study. The test series included 95 samples taken from patients treated surgically at different hospitals in the Oslo region (Table 1). These patients were selected to include approximately equal amounts of stage II and III tumors, equal amounts of survival events between the stages, as well as long term follow-up among survivors (>10 years). None of the patients received adjuvant chemotherapy. Tumor stage was the only clinical characteristic with significant association to patient survival (Table 3). The independent validation series was consecutively collected (95% inclusion rate) and consisted of 77 patients treated by curative resection at Aker University Hospital, Oslo. These patients received adjuvant treatment according to the current standard, i.e. routine administration of chemotherapy for patients presenting with stage III tumors. This series is further referred to as validation series I (Table 1). RNA was extracted from the samples using the Qiagen AllPrep DNA/RNA Mini Kit (Qiagen, BmbH, Hilden, Germany). Microsatellite instability (MSI)-status of the clinical specimens has previously been determined (Berg et al., PLoS One 5:e13978, 2010; Thorstensen et al., Gastroenterology 121:1275-1280, 2001).

The research biobanks have been registered according to national legislation, and the study has been approved by the Regional Committee for Medical Research Ethics (numbers 2781 and 236-2005-16141).

Additionally, publically available gene expression data from two independent series of altogether 215 stage II and III CRC patients were accessed from NCBI's Gene Expression Omnibus (GEO),[25] accession numbers GSE14333 and GSE17538. There was extensive overlap between samples in the two series (n=97 stage II and III samples from the H. Lee Moffitt Cancer Center). Only unique samples were included in the current study, and are herein referred to as validation series II. Clinical information for the patients was obtained from the respective GEO entries (Table 1).

Microarray Expression Analysis

One μg total RNA from each of the 172 samples were individually processed according to the Affymetrix GeneChip® Whole Transcript (WT) Sense Target Labeling Assay manual (Affymetrix Inc, Santa Clara, Calif.). Fragmented and labeled sense strand DNA was hybridized onto the Affymetrix GeneChip Human Exon 1.0 ST Array for 16-18 hours. This array contains 1.4 million probe sets of which 289,961 belong to the "core" set of probe sets targeting well annotated full-length human mRNAs (Affymetrix Inc: GeneChip Exon Array Design, 2009). Each gene is targeted by an average of 40 probes along the entire length of the coding sequence (corresponding to approximately 10 probe sets). Array washing, staining and scanning were performed according to the manufacturer's protocol.

Preprocessing of Gene Expression Data

Raw intensity data from scanned images of the microarrays were preprocessed by the Affymetrix GeneChip Command Console software (version 1.0). The expression intensities were stored as sample-wise cell intensity (CEL) files. Using the CEL-files as input, the robust multi-array average (RMA) algorithm was applied (Irizarry et al., Biostatistics 4:249-264, 2003) implemented in the Affymetrix Expression Console 1.1 software for inter-chip quantile normalization across each of the two patient series, and summarized the perfect match probes at the gene-level using the Affymetrix HuEx-1_0-st-v2.r2 gene-core library files. The library files defined 22,011 transcript clusters, of which 17,617 targeted annotated genes using the Affymetrix HuEx-1_0-st-v2.na31.hg19.transcript.csv annotation file. Parts of the microarray data have previously been published (Sveen et al., Genome Med 3:32, 2011) and can be accessed from GEO (GSE30378 and GSE24550). For the current study, twelve additional samples were included in the test series (GSM753769-GSM753780), and are amended to the GSE30378 record.

Gene-level expression data for validation series II, analyzed on Affymetrix HG-U133 Plus2.0 arrays, were downloaded as CEL-files from GEO (GSE14333 and GSE17538). The raw data were preprocessed using Affymetrix Expression Console 1.0. The CEL-files were background corrected, quantile normalized, and summarized with the RMA algorithm applying the Affymetrix HG-U133_Plus_2.cdf library file. Using the Affymetrix HG-U133_Plus_2. na31.annot.csv annotation file, a total of 54,675 probe sets targeting 41,779 transcripts from annotated genes were identified.

Development of the Prognostic Gene Expression Signature

A gene expression signature for prediction of prognosis was developed from the test series of 95 CRC samples. The gene expression dataset was filtered to include only genes with variances in expression levels higher than 0.2, and P-values (Wald test of predictive potential) from univariate Cox proportional hazards analysis lower than 0.5 (n=3,098 genes). This gene set was subjected to penalized multivariate Cox proportional hazards survival modeling using an algorithm for variable selection based on $L_1$ penalized (lasso) estimation (see below) (Goeman, Biom J 52:70-84, 2009). Using this model, the identity and number of genes selected to constitute the prognostic expression signature was determined via cross-validation in the test series. A penalty parameter, $\lambda_1$, reflecting the predictive potential and calculated by cross-validation, was inflicted upon the gene expression signals during survival modeling.

Genes in the resulting prognostic expression signature were considered to be associated with poor patient survival at expression levels above the 80$^{th}$ percentile across the dataset for genes with univariate hazard ratios (HR)>1, and below the 20$^{th}$ percentile for genes with univariate HR<1. To obtain a simple classification rule, patients were stratified into prognostic groups according to the number of genes in the prognostic signature being expressed at levels associated with poor prognosis. For comparison, sample-wise prognostic indices (PI) were also calculated based on expression values and lasso-penalized multivariate regression coefficients for genes in the signature, and used for prognostic stratification.

Statistical Analyses

Further statistical analyses were done using the SPSS 16.0 software (SPSS Inc, Chicago, Ill.). These include standard univariate and multivariate Cox proportional hazards analyses (estimation of HR and corresponding 95% confidence intervals (CI)), Wald test for predictive potential, generation of Kaplan-Meier survival plots, and Pearson correlation analysis. Two-sided P-values ≤0.05 were considered significant. For survival analyses, the end point was relapse-free survival. Relapse and death from CRC were regarded events, and patients with no events were censored. Generation of the correlation heatmap was done using J-Express 2011 (MolMine AS, Bergen, Norway).

Filtering of the Gene Expression Dataset from the Test Series

A genome-wide expression dataset of 17,617 genes from 95 stage II and III CRC samples, obtained from Affymetrix GeneChip Human Exon 1.0 ST arrays, was used as a test series for survival modeling. Since the prognostic value of the resulting gene expression signature was to be tested also in an independent patient series analyzed on Affymetrix HG-U133 Plus2.0 arrays (validation series II), only genes identifiable by gene symbols on both types of arrays were retained (n=15,851; annotation based on the human genome build GRCh37). This dataset was filtered to include only genes with expression variances higher than 0.2, and P-values from univariate Cox proportional hazards analyses below 0.5 (n=3,098 genes). P-values (Wald test of predictive potential) were calculated in R 2.11.1 using the Bioconductor package Weighted Gene Co-expression Network Analysis (WGCNA) (Langfelder et al., BMC Bioinformatics 9:559, 2008). Codes were retrieved from The Comprehensive R Archive Network (CRAN) web pages (Langfelder, P and Horvath, S: Package 'WGCNA', 2010).

Commands used to open the Bioconductor library and set up the working directory:
library(WGCNA)
setwd("A"), A=path to working folder.

Commands used to set up the data to be analyzed with univariate Cox proportional hazards analyses in the proper format:
time<-c(B, . . . , C), B=time to recurrence or censoring for sample 1, C=time to recurrence or censoring for sample 95.
event<-c(D, . . . , E), D=1 (recurrence) or 0 (censoring) for sample 1, E=1 (recurrence) or 0 (censoring) for sample 95.
datExpr<-t(as.matrix(read.table("M.txt", header=TRUE, sep="\t", row.names=1, as.is=TRUE))), M=tab-delimited gene expression signal matrix with sample headings and one column with probe set ids.

Commands used to run the univariate Cox proportional hazards analyses for the input data, and write the results to a tab-delimited text-file called 'univariateCox.txt':
c<-standardScreeningCensoredTime(time, event, datExpr, fastCalculation=F)

Analysis Workflow for Development of the Prognostic Gene Expression Signature

The filtered gene expression dataset from the test series of stage II and III CRCs was used as input for the Bioconductor package penalized (Goeman, J J: penalized: L1 (lasso) and L2 (ridge) penalized estimation in GLMs and in the Cox model, 2010). This analysis tool contains an algorithm for lasso penalized multivariate Cox proportional hazards modeling of survival data using gene expression signals, performing variable selection and shrinkage (Goeman et al., supra). The algorithm calculates a penalty parameter ($\lambda_1$) for the input variables based on leave-one out cross-validation of each of the 95 samples. The amount of genes to be included in the prognostic expression signature is a function of $\lambda_1$. The optimal $\lambda_1$-value corresponds to the best performing signature during cross-validation, i.e. resulting in the highest cross-validated partial likelihood. Applying higher $\lambda_1$-values will generally reduce the number of genes included in the prognostic expression signature, and the prediction will approach univariate estimation. At lower $\lambda_1$-values, the number of genes included in the signature increases, consequently increasing also the risk of overfitting the signature to the specific prognostic associations within the test data, and potentially reducing its predictive power. For the final step in the algorithm, the chosen $\lambda_1$-value was applied as a tuning parameter for lasso penalized modeling of the test dataset. The analyses were done using version 2.11.1 of R. R codes were retrieved from the CRAN web pages (Goeman, J J: Package 'penalized', 2010).

Commands used to open the Bioconductor library penalized and set up the working directory:
library(penalized)
setwd("A"), A=path to working folder.

Commands used to read and set up the input data:
s<-Surv(time, event), time and event are vectors as described in the previous section.
exprData<-t(as.matrix(read.table("D.txt", header=TRUE, sep="\t", row.names=1, as.is=TRUE))), D=tab-delimited gene expression signal matrix with sample headings and one column with probe set id's.

Commands used to calculate the penalty parameter for the gene expression data by leave-one-out cross-validation:
opt<-optL1(s, penalized=exprData, fold=10)

Commands used to return the results from the cross-validation at the optimal $\lambda_1$-value:
opt Commands used to run and return the results from survival modeling using penalized gene expression signals:
p<-penalized(s, penalized=exprData, lambda1=E), E=chosen $\lambda_1$
show(p)
coefficients(p)

Figure 4:
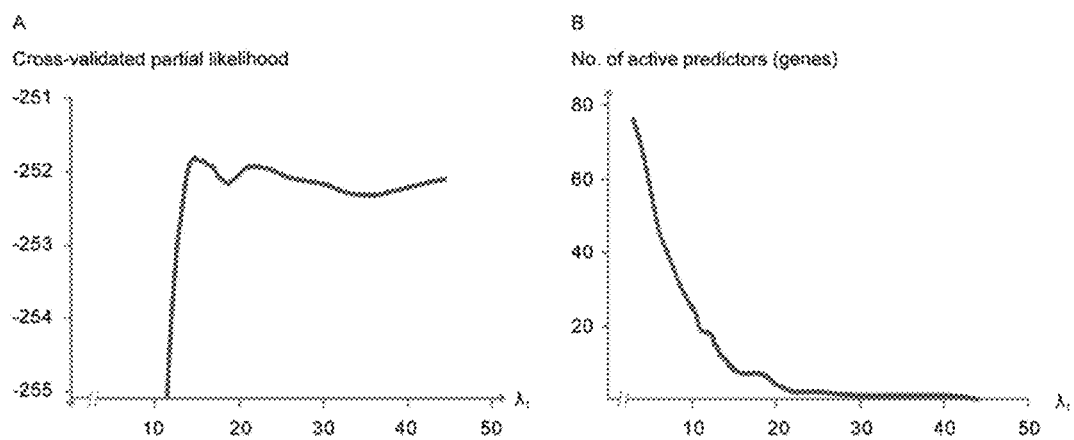
FIG. 4. Cross-validated partial likelihood and number of active predictors in the test series as a function of the penalty parameter. The lasso survival modeling algorithm using multivariate and penalized Cox proportional hazards analysis calculated A) the cross-validated partial likelihoods and B) the number of active prognostic predictors as a function of the penalty parameter $\lambda_1$ in the test series of colorectal cancers. The input data consisted of 3,098 genes with variances in expression levels higher than 0.2, and significance levels from univariate Cox proportional hazards analyses lower than 0.5, as well as information on 10-year relapse-free survival for the patients. The cross-validated partial likelihood represents the potential of the selected active predictors to predict patient survival, as calculated by leave-one out cross-validation, and indicating optimal prediction at high values. The distribution of cross-validated partial likelihoods achieved optimum (approximately −252) for several values of the penalty parameter $\lambda_1$>13, corresponding to selection of differently sized gene expression signatures with equal predictive potential (signatures ranging in size from 0 to 12 genes).

The survival modeling was repeated 1,000 times. By cross-validation during these iterations, several models were found to accommodate optimal prediction in the test series. The distribution of cross-validated partial likelihoods achieved an optimal value (approximately −252) for several values of $\lambda_1$>13, corresponding to gene expression signatures of various sizes (≤12 genes; FIG. 4). Across the iterations, seven different gene expression signatures were found to accommodate optimal survival prediction more than 50 times each (FIG. 1). The most frequently reported signature (n=202 times) included only one gene (OLFM4, $\lambda_1$ ranging from 30 to 44). Other optimal signatures included two, seven, eight, nine, eleven, or twelve genes ($\lambda_1$-values corresponding to no active predictors ($\lambda_1 \geq 44$) were also reported). All genes within the smaller signatures were included also in the larger signatures (no gene replacements). The $\lambda_1$-values for the reported signatures ($\lambda_1 \geq 13$) were all associated with the optimal cross-validated partial likelihood. For all these signatures, except the 1-gene signature, there were significant associations between patient survival and increasing numbers of genes expressed at levels associated with poor survival (genes were considered to be associated with poor patient survival at expression levels above the $80^{th}$ percentile across the dataset for genes with univariate HR>1, and below the $20^{th}$ percentile for genes with univariate HR<1). The HR (univariate Cox proportional hazards analyses for the 2-gene, 7-gene, 8-gene, 9-gene, 11-gene, and 12-gene signatures) ranged from 1.6 to 1.9 (P<0.04). Further, dichotomization of patients to good and poor prognosis groups was tested for all possible stepwise increases in amounts of genes with associations to poor survival within each signature (FIG. 1, heatmap in lower panel). For the 28 possible poor prognosis groups, 22 had significant associations with poor patient survival (univariate Cox proportional hazards analyses, HR ranging from 3.0 to 11.5; P<0.04).

To assess which stratification rule had the best predictive potential on independent samples, the same patient stratification according to the different gene signatures were repeated in validation series I. Here, five of the dichotomizing stratification rules resulted in significant prognostic stratification (univariate Cox proportional hazards analyses, HR ranging from 2.9 to 5.8; P<0.04). The best performing stratification rule across both series (by rank of P-values from univariate Cox proportional hazards analyses), assigned patients to a poor prognosis group when expressing three or more genes in the 7-gene signature at levels associated with poor prognosis. In the test series, 23% of the patients were assigned to the poor prognosis group by this stratification rule, while 17% of patients were predicted to have poor prognosis in validation series I. By the other four stratification rules having significant associations with patient survival also in validation series I, only ≤6% of the patients were predicted to have poor survival. Hence, for further assessment of prognostic predictive potential, the 7-gene signature was used.

As an inherent part of the lasso survival model, penalized multivariate regression coefficients were calculated for each gene in the 7-gene signature (Table 4; penalty parameter $\lambda_1$=16). Using these regression coefficients, and the corresponding gene expression values, a prognostic index (PI) was calculated for each patient:

PI=[(expression value)$_{Gene1}$·(regression coefficient)$_{Gene1}$]+[(expression value)$_{Gene2}$·(regression coefficient)$_{Gene2}$]+

For comparative purposes, the PIs were used to stratify patients according to prognosis, and high PIs indicated poor prognosis.

In validation series II, analyzed on Affymetrix HG-U133 Plus2.0 arrays, there were 12 probe sets targeting the seven genes in the optimal expression signature developed. For redundant probe sets, the sample-wise median expression value was used (Supplementary Table 2).

Assessment of the 7-Gene Signature

In all three patient series, there was a 'dose-effect' between amounts of genes in the 7-gene signature predicting poor survival and patient survival rates. That is, the sample-wise increase in amounts of genes with expression levels associated with poor survival (sample-wise amounts ranged from zero to four in the test series, and zero to five in the two validation series) was associated with increasingly poorer patient survival. In the test series, the univariate HR was 1.8 ([1.5, 2.3]; P<0.001, Wald test for predictive potential). The corresponding HR in validation series I and II were 1.5 [1.0, 2.1] and 1.6 [1.3, 2.1], respectively (P=0.04 and <0.001, respectively).

For comparison, sample-wise PIs were calculated based on expression values and lasso-penalized multivariate regression coefficients for genes in the 7-gene signature. The PIs ranged from −0.2 to 1.4, −0.06 to 1.50, and −0.5 to 0.9 in the test series and validation series I and II, respectively. Univariate Cox proportional hazards analyses for the PIs showed significant survival stratification in all three series (HR=17.7 [6.7, 46.7], 4.3 [1.2, 16.1], and 4.7 [1.6, 13.8], respectively; P<0.03). To further compare these results to the stratification rule based on counting the sample-wise numbers of genes in the 7-gene signature with associations with poor prognosis, patients were dichotomized by assigning patients with PI>$80^{th}$ percentile of PIs across the individual series to poor prognosis groups (to simulate the assignment of approximately 20% of patients to poor prognosis groups when expressing three or more of the seven genes at levels associated with poor prognosis). The univariate HRs for the test series and validation series I and II were 4.1 [2.2, 7.5], 2.1 [0.8, 5.5], and 2.6 [1.4, 4.7], respectively (P≤0.001, 0.1, and 0.003, respectively). Hence, the performance of the 7-gene signature was similar for stratification based on sample-wise amounts of genes being expressed at levels associated with poor survival and PI-calculations, indicating that the much simpler principle used for stratification in the former approach was a valid replacement for the commonly used regression model strategy in the latter approach.

R Code for Calculating and Plotting Density Distributions

For plotting purposes (FIG. 5), density distributions of expression signals for genes in the prognostic signature were calculated for patients in the test series using the Bioconductor package sm[44]. The appropriate R code was retrieved from the CRAN web pages[45].

Commands for opening the Bioconductor library and setting up the input data:

library(sm)

variable<-c(A, B), A=gene expression signal for patient 1, B=gene expression signal for patient 95.

C<-c(D, E), D=1 for event (recurrence), or 0 for censoring for patient 1, E=1 for event (recurrence), or 0 for censoring for patient 95.

This command was used to calculate and plot the density estimates of expression signals for the two assigned groups individually:

sm.density.compare(variable, group=C)

Results

Development of the Prognostic Gene Expression Signature

Lasso-penalized multivariate Cox proportional hazards modeling was performed on a filtered genome-wide expression dataset obtained from a test series of 95 stage II and III CRCs. There were several survival models accommodating optimal penalty conditions from cross-validation (FIG. 4). Across 1,000 iterations, seven different gene expression signatures accommodated optimal survival prediction in the test series more than 50 times each (size range 1 to 12 genes; FIG. 1). These different signatures expanded on the same sets of genes, and the smaller signatures were subsets of the larger.

Figure 2:
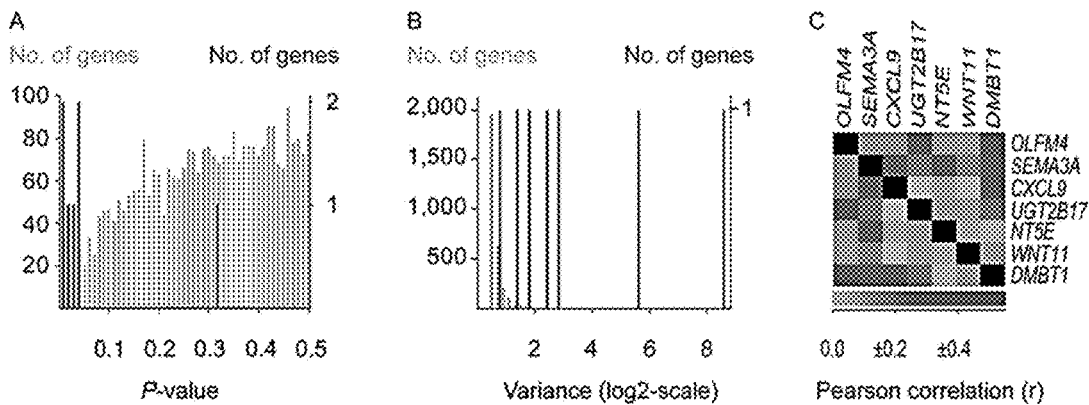
FIG. 2. Statistical characteristics of genes in the prognostic expression signature. The seven genes in the expression signature had A) low P-values from univariate Cox proportional hazards analyses (median P=0.02, Wald test for predictive potential), and B) high variances in gene expression signals (median 2.4, log 2-scale), compared to the remaining 3,091 genes included for survival modeling (grey; median P=0.3; median variance 0.3). C) The Pearson correlations of expression signals between the seven genes in the signature were generally weak (absolute values ranging from 0.006 to 0.55).
Figure 5:
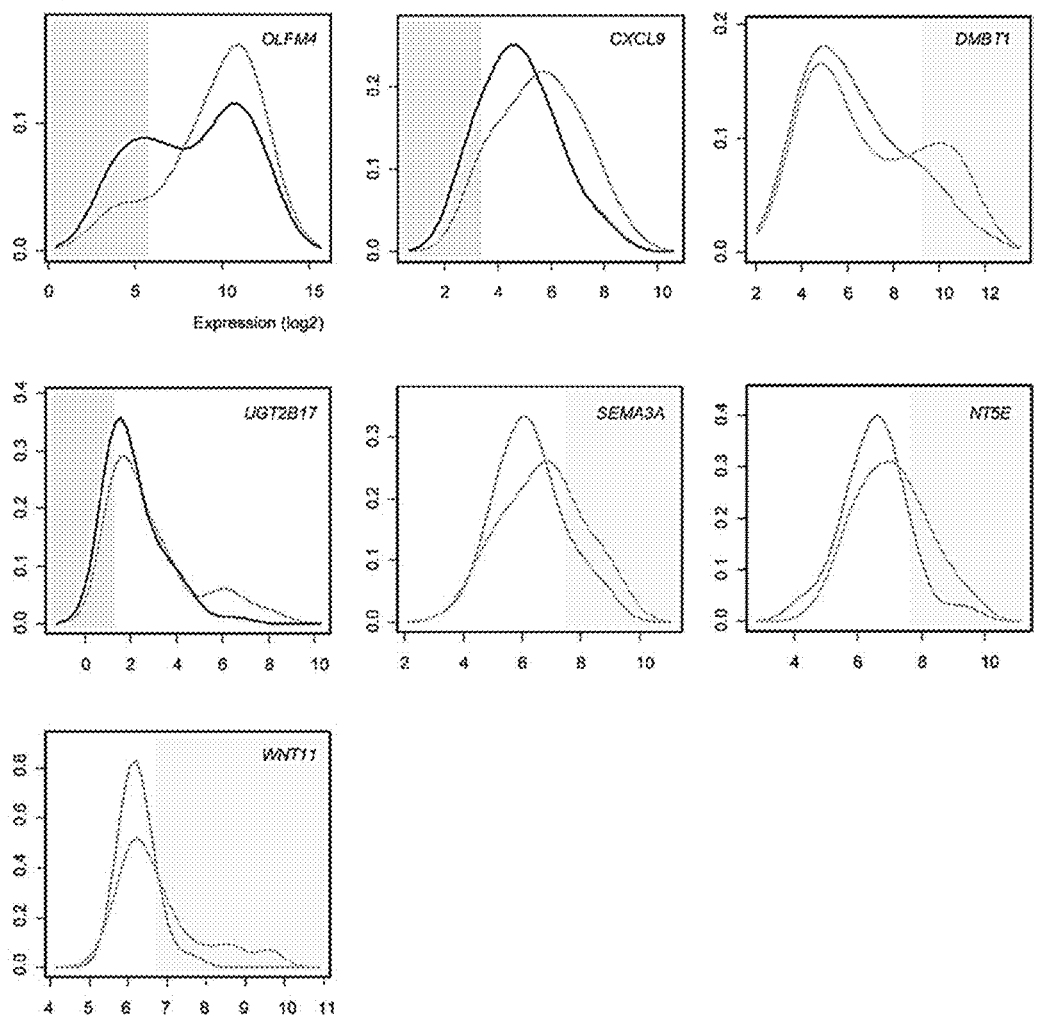
FIG. 5. Expression of genes in the 7-gene prognostic signature in the test series. Density measures of relative amounts of samples are plotted versus gene expression (log-2 transformed).

To further assess which signature had the best predictive potential in independent samples, these signatures were tested also in validation series I. The best performing stratification rule across the test series and validation series I assigned patients to a poor prognosis group when expressing (any) three or more genes in the 7-gene signature at levels associated with poor prognosis (FIG. 5). The genes included in the signature were OLFM4, CXCL9, DMBT1, UGT2B17, SEMA3A, NT5E, and WNT11 (Table 4). In accordance with the initial selection criteria for genes entered into the lasso algorithm, and the algorithm itself, the seven genes had strong univariate associations with patient survival in the test series, as well as large variation and low correlation in gene expression (FIG. 2).

Assessment of the Prognostic Gene Expression Signature

The performance of the 7-gene expression signature was assessed on stage II and III CRC patients in the test series (n=95), and both independent validation series I and II (n=77 and 215, respectively). Patients with increasing amounts of genes with expression levels indicating poor survival (sample-wise amounts ranged from zero to four in the test series, and zero to five in the two validation series), had increasingly poorer survival in all three series (HR≥1.5, P≤0.04, Wald test for predictive potential).

Figure 3:
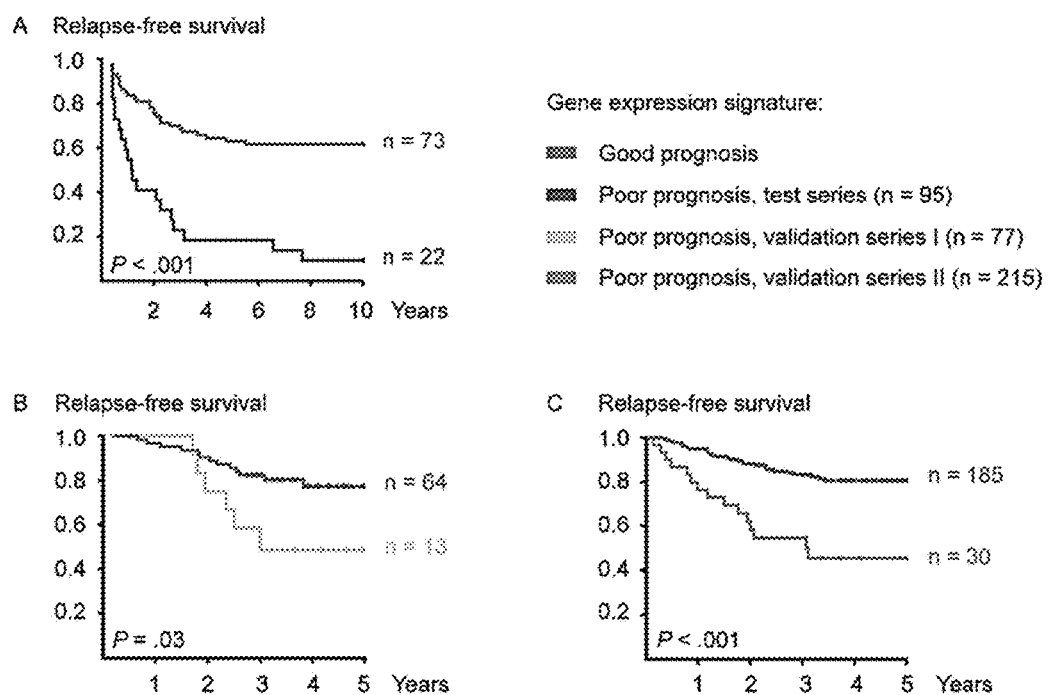
FIG. 3. Survival curves for stage II and III CRC patients in the three independent series stratified by the 7-gene expression signature. A) Patients in the test series assigned to the poor prognosis group had a 10-year relapse-free survival rate of 9%, significantly poorer than the 62% survival rate for patients in the good prognosis group. The corresponding 5-year survival rates for patients in B) validation series I and C) validation series II, were 49% compared to 78%, and 46% compared to 81%, respectively.

The assignment of patients to a poor prognosis group when expressing three or more of the seven genes at levels associated with poor survival resulted in significant prognostic stratification in all three patient series (FIG. 3). In the test series, 23% of the patients (22 of 95) were assigned to the poor prognosis group. These patients had a 10-year relapse-free survival rate of 9%, compared to 62% for patients with good prognosis (univariate HR=4.0; 95% CI, 2.2 to 7.2, P<0.001, Wald test of predictive potential). In validation series I and II, 17% and 14% of the patients were assigned to the poor prognosis group (13 of 77 patients, and 30 of 215 patients), respectively. Poor prognosis patients in validation series I had a 5-year relapse-free survival rate of 49%, compared to 78% for patients in the good prognosis group (univariate HR=2.9 [1.1, 7.5]; P=0.03). The corresponding survival rates in validation series II were 46% and 81%, respectively (univariate HR=3.8 [2.1, 7.1]; P<0.001). The prognostic value of the expression signature was confirmed by evaluating the performance of the corresponding PI's. The 20% of the patients with highest PI's had markedly poorer survival than the rest of the patients. The univariate HR's for the test series and validation series I and II were 4.1 [2.2, 7.5], 2.1 [0.8, 5.5], and 2.6 [1.4, 4.7], respectively (P≤0.001, 0.1, and 0.003, respectively).

The gene expression signature was also an independent predictor of poor patient survival in multivariate models including tumor stage and other clinic-pathological parameters. Multivariate HRs were 4.1 [2.2, 7.5], 3.8 [1.1, 12.7], and 3.2 [1.7, 6.0], in the test series (Supplementary Table 1) and validation series I and II (Table 2), respectively (P<0.001, 0.03, and 0.001, respectively). Patients were also correctly stratified according to survival within each stage. (FIG. 6).

TABLE 1

Clinicopathological and molecular characteristics of the independent CRC sample series

| Characteristic | Test series (n = 95) | Validation series I (n = 77) | Validation series II* (n = 215) |
|---|---|---|---|
| Age at diagnosis (mean ± SD) | 66 ± 11.7 | 73 ± 13.5 | 66 ± 13.3 |
| Gender | | | |
| Male | 46 | 33 | 115 |
| Female | 49 | 44 | 100 |
| Stage | | | |
| II | 52 | 44 | 108 |
| III | 43 | 33 | 107 |
| Location | | | |
| Right | 27 | 46 | 85 |
| Left | 31 | 20 | 77 |
| Rectum | 37 | 11 | 22 |
| Unknown | | | 31 |
| Mean follow-up, years (minimum; maximum) | 5.9 (0.3; 10) [†] | 3.3 (0.2; 5) [‡] | 3.1 (0.04; 5.0) [‡] |
| No. of events, stage II[§] | 21 | 9 | 13 |
| No. of events, stage III[§] | 27 | 10 | 32 |
| MSI | | | |
| MSI-high | 7 | 14 | NA |
| MSI-low | 8 | 10 | NA |
| Adjuvant chemotherapy (mainly stage III) | None | Yes | Yes |
| Collection year | 1987-1989 | 2005-2007 | NA |

*GEO accession numbers GSE14333 and GSE17538. Only non-overlapping samples from stage II and III patients were included
[†] Ten years follow-up
[‡] Five years follow-up
[§] Relapse or death from CRC.
Abbreviations: MSI, microsatellite instability; NA, not available; SD, standard deviation

TABLE 2

Prognostic stratification of stage II and III CRC patients in the two independent validation series by the 7-gene expression signature

| | Validation series I | | | | Validation series II* | | | |
|---|---|---|---|---|---|---|---|---|
| | Univariate | | Multivariate | | Univariate | | Multivariate | |
| Variable | HR[†] [95% CI] | P-value[‡] | HR[†] [95% CI] | P-value[‡] | HR[†] [95% CI] | P-value[‡] | HR[†] [95% CI] | P-value[‡] |
| Gene expression signature | 2.9 [1.1, 7.6] | .03 | 3.8 [1.1, 12.7] | .03 | 3.8 [2.1, 7.1] | <.001 | 3.2 [1.7, 6.1] | <.001 |
| Tumor stage | 1.8 [0.7, 4.3] | .2 | 0.9 [0.3, 3.2] | .9 | 2.7 [1.4, 5.2] | .002 | 2.4 [1.2, 4.6] | .01 |
| MSI-H[§] | 5.3 [0.7, 40.1] | .1 | 9.7 [0.8, 114.3] | .07 | NA | NA | NA | NA |
| Tumor grade** | 0.4 [0.1, 1.5] | .2 | 0.07 [0.009, 0.5] | .007 | NA | NA | NA | NA |

TABLE 2-continued

Prognostic stratification of stage II and III CRC patients in the two independent validation series by the 7-gene expression signature

| | Validation series I | | | | Validation series II* | | | |
|---|---|---|---|---|---|---|---|---|
| | Univariate | | Multivariate | | Univariate | | Multivariate | |
| Variable | HR† [95% CI] | P-value‡ | HR† [95% CI] | P-value‡ | HR† [95% CI] | P-value‡ | HR† [95% CI] | P-value‡ |
| Tumor location†† | 1.7 [0.9, 2.9] | .08 | 1.4 [0.7, 2.8] | .4 | 1.1 [0.7, 1.7] | .6 | 1.2 [0.8, 1.9] | .4 |
| Age at diagnosis | 1.0 [0.9, 1.0] | .2 | 1.0 [1.0, 1.0] | .8 | 1.0 [1.0, 1.0] | .3 | 1.0 [1.0, 1.0] | .6 |
| Gender‡‡ | 1.3 [0.5, 3.3] | .5 | 1.5 [0.5, 4.5] | .4 | 1.1 [0.6, 2.0] | .8 | 1.0 [0.5, 1.8] | 1.0 |

*GEO accession numbers GSE14333 and GSE17538 (n = 215)
†HRs and corresponding 95% CIs from univariate or multivariate Cox proportional hazards analysis as indicated. Event = relapse or death from CRC within five years. Censoring = no event or lost to follow-up within five years
‡P-values from Wald test of predictive potential
§1 = high degree of MSI, 2 = low degree of MSI, or microsatellite stable
**1 = low grade (n = 5), 2 = medium grade (n = 69), 3 = high grade (n = 3)
††1 = right side, 2 = left side, 3 = rectum
‡‡1 = female, 2 = male.
Abbreviations: CI, confidence interval; HR, hazard ratio; MSI, microsatellite instability; NA, not available

TABLE 3

Cox proportional hazards analyses for patients in the test series

| | Univariate Cox | | Multivariate Cox | |
|---|---|---|---|---|
| Clinical characteristic | HR (95% CI)* | P-value† | HR (95% CI)* | P-value† |
| Gene expression signature | 4.0 [2.2, 7.2] | <.001 | 4.1 [2.2, 7.5] | <.001 |
| Tumor stage | 2.0 [1.1, 3.6] | .02 | 2.3 [1.2, 4.2] | .008 |
| MSI‡ | 2.6 [0.6, 10.6] | .2 | 4.2 [0.9, 18.3] | .06 |
| Tumor location§ | 1.0 [0.7, 1.4] | .9 | 1.0 [0.7, 1.5] | 1.0 |
| Age at diagnosis | 1.0 [1.0, 1.0] | .2 | 1.0 [1.0, 1.0] | .4 |
| Gender** | 0.9 [0.5, 1.5] | .6 | 0.7 [0.4, 1.3] | .3 |

*HRs and corresponding 95% CIs from univariate or multivariate Cox proportional hazards analysis as indicated. Event = relapse or death from CRC within ten years. Censoring = no events within ten years
†P-values from Wald test of predictive potential
‡1 = MSI-high, 2 = MSS or MSI-low
§1 = right side, 2 = left side, 3 = rectum
**1 = female, 2 = male.
Abbreviations: CI, confidence interval; HR, hazard ratio; MSI, microsatellite instability; MSS; microsatellite stability

TABLE 4

Genes in the prognostic expression signature

| Gene symbol | Full name | Function | Cytogenetic band | Exon array ID*, Gene array ID† | Univariate HR‡, Penalized multivariate regression coefficient§ |
|---|---|---|---|---|---|
| OLFM4 | Olfactomedin 4 | Indications as an antiapoptotic factor promoting tumor growth, and also facilitating cell adhesion | 13q14.3 | 3490892, 212768_s_at | 0.91, −0.08 |
| CXCL9 | Chemokine (C-X-C motif) ligand 9 | Involvement in T cell trafficking and affects the growth, movement, or activation state of cells that participate in immune and inflammatory responses | 4q21.1 | 2773947, 203915_at | 0.79, −0.10 |
| DMBT1 | Deleted in malignant brain tumors 1 | Candidate tumor suppressor gene for brain, lung, esophageal, gastric, and colorectal cancers | 10q26.1 | 4037778, 208250_s_at | 1.06, 0.04 |
| UGT2B17 | UDP glucuronosyltransferase 2 family, polypeptide B17 | Enzyme catalyzing the transfer of glucuronic acid from uridine diphosphoglucuronic acid to a diverse array of substrates including steroid hormones and lipid-soluble drugs. Glucuronidation is an intermediate step in the metabolism of steroids | 4q13.2 | 2772088, 207245_at | 0.78, −0.02 |
| SEMA3A | Sema domain, immunoglobulin domain (Ig), short basic domain, secreted, (semaphorin) 3A | This secreted protein can function as either a chemorepulsive agent, inhibiting axonal outgrowth, or as a chemoattractive agent, stimulating the growth of apical dendrites. Increased expression of this protein is associated with schizophrenia and is seen in a variety of human tumor cell lines | 7p12.1 | 3059464, 206805_at & 244163_at & 244849_at | 1.33, 0.10 |

TABLE 4-continued

Genes in the prognostic expression signature

| Gene symbol | Full name | Function | Cytogenetic band | Exon array ID*, Gene array ID [†] | Univariate HR[‡], Penalized multivariate regression coefficient[§] |
|---|---|---|---|---|---|
| NT5E | 5'-nucleotidase, ecto | Hydrolyzes extracellular nucleotides into membrane permeable nucleosides | 6q14.3 | 2915828, 1553994_at & 1553995_a_at & 203939_at & 227486_at | 1.43, 0.05 |
| WNT11 | Wingless-type MMTV integration site family, member 11 | The WNT gene family consists of structurally related genes which encode secreted signaling proteins. These proteins have been implicated in oncogenesis, e.g. in colorectal cancer, and in several developmental processes, including regulation of cell fate and patterning during embryogenesis | 11q13.5 | 3382523, 206737_at | 1.62, 0.10 |

*Affymetrix GeneChip Human Exon 1.0 ST array transcript cluster ID
[†] Affymetrix HG-U133 Plus2.0 array probe set ID. For genes targeted by multiple probe sets, the median expression value was used
[‡] Hazard ratios (HR) from univariate Cox proportional hazards analysis in the test series of colorectal cancers
[§] Regression coefficients from the lasso model at $\lambda_1 = 16$

Example 2

This example describes the confirmation of the microarray results using real-time quantitation of gene expression using a TaqMan™ assay as well as identification of genes that can be substituted for genes in the original 7 gene panel. ColoGuidePRO was developed by expression data from Affymetrix microarrays (GeneChip® Human Exon 1.0 ST), and the transferability to other gene expression platforms has been demonstrated by analysing the same genes in 19 stage II and 20 stage III colorectal cancer samples by both microarrays and by real-time RT-PCR. This is not intended to be the final RT-PCR-based classifier, but a preliminary model established for the purpose of demonstrating the feasibility of the RT-PCR-based approach as such, and the general robustness of ColoGuidePRO in terms of transferability to other expression platforms.

Briefly, TaqMan™ primers and probes were selected and tested for the 7 gene panel, and control genes. Assay identifiers are provided in Table 5 below.

TABLE 5

TaqMan Assay identifiers.

| ColoGuidePro | CXCL9 | Hs00171065_m1 |
|---|---|---|
| | DMBT1 | Hs01069306_m1 |
| | NT5E | Hs00159686_m1 |
| | OLFM4 | Hs00197437_m1 |
| | SEMA3A | Hs00173810_m1 |
| | UGT2B17 | Hs00854486_sH |
| | WNT11 | Hs00182986_m1 |
| Control genes | GPX1 | Hs00829989_gH |
| | ATP5E | Hs00855401_g1 |
| | VDAC2 | Hs00748551_s1 |
| | TBP | Hs99999910_m1 |
| | RPLP0 | Hs99999902_m1 |
| | PES1 | Hs00362795_g1 |
| | ADAMTS20 | Hs00228033_m1 |
| | CAPN10 | Hs00225048_m1 |
| | NPHP4 | Hs00296416_m1 |

Expression levels of each of the 7 genes were assessed by TaqMan assays, and Pearson correlation coefficients (r) between microarray and RT-PCR data are shown in Table 6 alongside with associated p-values. All genes had r>0.75 and p-values <0.0001.

TABLE 6

Correlations coefficients for individual genes

| ColoGuidePro (39 stage II and III samples from two patient series) | OLFM4 | −0.96 | 1.47E−21 |
|---|---|---|---|
| | CXCL9 | −0.85 | 7.57E−12 |
| | DMBT1 | −0.93 | 5.77E−17 |
| | UGT2B17 | −0.89 | 1.80E−11 |
| | SEMA3A | −0.76 | 2.41E−08 |
| | NT5E | −0.83 | 4.16E−11 |
| | WNT11 | −0.76 | 2.47E−08 |

The reagents in Table 5 were used to analyze gene expression levels in patient samples. The results are presented in FIG. 7.

The plot shows a good correspondence between qPCR and exon microarray data in the sample-wise number of genes in ColoGuidePro being expressed at levels associated with poor prognosis. Since only a subset of the samples have been analyzed with qPCR at present (19 stage II samples and 20 stage III samples), the final thresholds for designating gene expression levels as associated with poor prognosis are not determined.

In the classification presented here, expression level thresholds for the qPCR data was set to classify the same amount of patients with poor prognosis per gene as for the exon microarray data within each stage. Assigning patients to the poor prognosis group when expressing 3 or more of the 7 genes in ColoGuidePro at levels associated with poor prognosis (the threshold used for microarray data), results in classification of 16 of 19 stage II patients (84%), and 16 of 20 stage III patients (80%) to the same category by qPCR and exon microarray data.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

The invention claimed is:

1. A method for amplifying a set of mRNA sequences from a tumor tissue sample from a human subject that has been previously diagnosed with stage III colorectal cancer, comprising:
   a) isolating and reverse transcribing mRNA from a tumor tissue sample from a human subject that has been previously diagnosed with stage III colorectal cancer to provide complementary DNA
   b) contacting said complementary DNA with primers specific for three or more complementary cDNAs selected from the group consisting of complementary cDNAs corresponding to OLFM4, CXCL9, DMBT1, UGT2B17, SEMA3A, NT5E, and WNT11 mRNAs and amplifying said complementary DNAs by polymerase chain reaction; and
   c) quantifying the level of expression of at least three of said OLFM4, CXCL9, DMBT1, UGT2B17, SEMA3A, NT5E, and WNT11 mRNAs relative to control samples.

2. The method of claim 1, wherein said tumor tissue sample is a biopsy sample.

* * * * *